US005194166A

United States Patent [19]

Burt et al.

[11] Patent Number: 5,194,166

[45] Date of Patent: Mar. 16, 1993

[54] PHOSPHOROUS AMINE LUBRICANT ADDITIVES

[75] Inventors: Gerald D. Burt, Moreland Hills; Randolph A. McDonald, Berea, both of Ohio

[73] Assignee: The Elco Corporation, Cleveland, Ohio

[21] Appl. No.: 911,839

[22] Filed: Jul. 10, 1992

Related U.S. Application Data

[62] Division of Ser. No. 526,080, May 18, 1990, Pat. No. 5,130,036.

[51] Int. Cl.$^5$ ................ C10M 137/02; C10M 139/00; C07F 9/02

[52] U.S. Cl. .................................. 252/32.5; 252/49.8; 558/72; 558/81; 558/169

[58] Field of Search ........................... 558/169, 72, 81; 252/32.5, 49.9, 49.8

[56] References Cited

U.S. PATENT DOCUMENTS

| | | | |
|---|---|---|---|
| 3,553,131 | 1/1971 | Hepplewhite et al. | 252/46.7 |
| 4,400,284 | 8/1983 | Jessup et al. | 252/49.6 |
| 4,427,560 | 1/1984 | Holstedt et al. | 252/42.7 |
| 4,490,265 | 12/1984 | Holstedt et al. | 252/47.5 |
| 4,522,629 | 6/1985 | Horodysky et al. | 44/315 |
| 4,529,528 | 7/1985 | Horodysky | 252/49.6 |
| 4,532,057 | 7/1985 | Horodysky et al. | 252/49.8 |
| 4,533,480 | 8/1985 | Holstedt et al. | 252/46.4 |
| 4,555,353 | 11/1985 | Horodysky et al. | 252/49.6 |
| 4,557,843 | 12/1985 | Holstedt et al. | 252/46.4 |
| 4,557,844 | 12/1985 | Horodysky | 252/49.9 |
| 4,557,845 | 12/1985 | Horodysky et al. | 252/49.9 |
| 4,587,026 | 5/1986 | Horodysky | 252/47.5 |
| 4,778,610 | 10/1988 | Horodysky | 252/32.5 |
| 4,857,214 | 8/1989 | Papay et al. | 252/32.5 |
| 4,965,002 | 10/1990 | Brannen et al. | 252/32.5 |

FOREIGN PATENT DOCUMENTS 152677 8/1985 European Pat. Off. .

*Primary Examiner*—Prince Willis, Jr.
*Assistant Examiner*—Alan D. Diamond
*Attorney, Agent, or Firm*—Panitch Schwarze Jacobs & Nadel

[57] ABSTRACT

Lubricant additives are produced by reacting an alkoxylated amine with phosphorous acid. The additives preferably also contain a boron moiety which is reacted with the phosphorous acid and amine, preferably in a one step reaction. More preferably, a mono-functional alcohol or a long-chain aliphatic carboxylic acid is added to this mixture. The additives are particularly useful in metal working oils and particularly as extreme pressure additives to replace the currently used chlorinated paraffin additives.

12 Claims, No Drawings

PHOSPHOROUS AMINE LUBRICANT ADDITIVES

CROSS-REFERENCE TO RELATED APPLICATIONS

The present application is a division of U.S. patent application Ser. No. 07/526,080 filed May 18, 1990, now U.S. Pat. No. 5,130,036, which is related to our copending patent application Ser. No. 148,828, filed Jan. 27, 1988, entitled "Phosphite Amine Lubricant Additives".

FIELD OF THE INVENTION

The present invention relates to reaction products of alkoxylated amines and phosphorous acid useful as lubricant additives. More particularly, the invention is directed to lubricant additives which can replace conventional chlorinated paraffins in applications such as extreme pressure metalworking.

BACKGROUND OF THE INVENTION

Chlorinated paraffin waxes, particularly higher molecular weight solid or liquid chlorinated paraffins in the $C_{10}$ to $C_{30}$ range have been widely used for over fifty years in metalworking uses, particularly as lubricant additives in drawing oils, extrusion oils and soluble oils, and particularly for extreme pressure applications. The largest volume is in drawing oils where chlorinated waxes are used almost exclusively, mainly in mineral oils. In extrusion oils, the additives usually include phosphorous and sulfur compounds due to the severity of operations. In soluble oils the chlorinated waxes are usually used in combination with fats or lard oils.

In 1977, twenty percent (40,000 tons) of the free-world production of liquid chlorinated paraffins was used in oil applications. However, in recent years, concern has arisen regarding toxicity and possible carcinogenicity of chlorinated paraffins. With the banning of chlorinated waxes in Germany and Canada, and the requirement of placing warning labels on drums of these materials in this country, alternative lubricant additives are being sought.

While many in the metalworking industry have switched to chlorinated olefins and polyesters, there is a concern among some that these chlorinated products as well may have carcinogenic properties. Hence, non-chlorinated substitutes are considered desirable. While sulfonated products have been satisfactory for light machining applications, they have not been generally satisfactory for heavier machining, such as the severe metal cuts and draws for which the chlorinated paraffins have been favored.

In the past, a number of non-chlorine containing additives have been developed to provide lubricating oil compositions with enhanced friction characteristics for use in engine and machinery lubricating oils and fuels. Such additives have included phosphorous compounds such as metal phosphonates, alkali metal salts of alkylphosphonic acids, and dihydrocarbyl hydrocarbylphosphonates; amines, such as alkoxylated amines; and certain boron-containing compounds. Examples of these prior art lubricating oil additives are discussed, for example, at column 1 of U.S. Pat. No. 4,529,528.

Published European Patent Application 152,677 discloses borated alkoxylated amines as thickeners for water based functional fluids. Borated alkoxylated amines are also disclosed in U.S. Pat. Nos. 4,400,284; 4,427,560; 4,490,265; 4,533,480 and 4,557,843 of Union Oil Company as intermediates for extreme pressure, anti-wear additives in lubricating compositions.

A series of additives has also been developed by Mobil Oil Corporation which are reaction products (essentially mixtures of simple and complex esters) of organic amines and organic phosphonates or phosphites. Early examples of such compositions are disclosed in U.S. Pat. No. 3,553,131 of Hepplewhite, et al., in which $C_6$–$C_{40}$ diaryl phosphonates (phosphites) are reacted with primary, secondary, or tertiary organic amines to produce products or mixtures which are incorporated in ester lubricants which are alleged to have higher load-carrying properties, surprising stability under storage and are relatively non-corrosive to metals.

A more recent series of patents to Horodysky, et al., assigned to Mobil, has disclosed engine lubricant and fuel additives which are the reaction product of a phosphorous compound, particularly a $C_1$–$C_6$ dihydrocarbyl phosphite, with an alkoxylated amine or a vicinal diol, with or without a boron compound, such as boric oxide, a metaborate, boric acid, or an alkyl borate. See, for example, U.S. Pat. Nos. 4,529,528; 4,557,845; 4,557,844; 4,555,353; 4,532,057 and 4,522,629. Mobil U.S. Pat. No. 4,587,026 also discloses borated N,N-bis(2-hydroxypropyl)cocamine in the presence of dodecyl phenol sulfide to give a friction-reducing, high temperature stabilizing additive.

While the reaction products of Heppelwhite and Horodysky, et al. are disclosed as possible additives for use with engine lubricating oils or greases, and a additives to liquid fuels such as gasoline, fuel oil and diesel oil, there is no disclosure of using these compounds for the severe requirements of metalworking fluid additives. Moreover, tests by the present inventors of several of the Horodysky, et al. products have shown serious disadvantages to the use of such products as additives to metalworking fluids, particularly in extreme pressure (EP) applications.

U.S. Pat. No. 4,857,214 also discloses phosphorous-containing compounds useful as additives in lubricants. The compounds of this reference comprise the oil soluble reaction product of an inorganic phosphorous acid or anhydride, a boron compound and an ashless dispersant. The preferred acid is phosphorous acid. The ashless dispersant may be, e.g., a hydrocarbyl succinimide, a mixed ester/amide of hydrocarbyl-substituted succinic acid, hydroxyesters of hydrocarbyl-substituted succinic acid, and the Mannich condensation products of hydrocarbyl-substituted phenols, formaldehyde and polyamines. Additional sources of nitrogen such as N-tallow diethanolamine may also be used in combination with the ashless dispersant. However, there is no disclosure of using the reaction product of an alkoxylated amine and phosphorous acid as a metalworking lubricant additive.

BRIEF SUMMARY OF THE INVENTION

According to the present invention, a lubricant additive is provided which is the reaction product of phosphorous acid with an alkoxylated amine of the formula

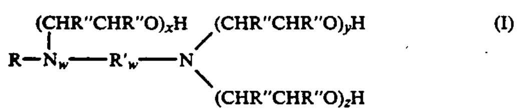

wherein R is a $C_6$ to $C_{30}$ hydrocarbon group or an alkoxylated $C_6$ to $C_{30}$ hydrocarbon group, R' is a $C_1$ to $C_6$ alkylene group and R'' is individually hydrogen or a $C_1$ to $C_6$ hydrocarbon group, w is 0 or 1 and x, y and z are each integers of from 0 to 10, at least one of which is not 0, preferably about 1 to 3, and more preferably each is 1.

Preferably, a boron compound selected from boric oxide, a metaborate or a compound of the formula $$(R^3O)_mB(OH)_n \quad (II)$$

wherein $R^3$ is a $C_1$ to $C_6$ alkyl group, and m and n are 0 to 3, their sum being 3, is included in the reaction with the alkoxylated amine and phosphorus acid to form the reaction product.

More preferably, an alcohol of the formula $$R^4OH \quad (III)$$

or a long-chain aliphatic carboxylic acid of the formula $$R^5\underset{\displaystyle O}{\overset{}{\underset{\|}{C}}}OH \quad (IV)$$

wherein $R^4$ and $R^5$ may each be a $C_1$ to $C_{30}$ hydrocarbon group, may be included in the reaction of the alkoxylated amine and phosphorous acid or the alkoxylated amine, phosphorous acid and boron compound to form a reaction product.

The present invention also includes lubricating oil compositions, particularly metal-working oils, containing the above-discussed reaction products as additives. These lubricating compositions may include a the major component mineral oils or synthetic oils including so-called "soluble oils" for use in forming aqueous emulsion lubricants. The invention also includes the use of the lubricant additives in metalworking operations, particularly extreme pressure operations.

DETAILED DESCRIPTION OF THE PREFERRED EMBODIMENTS

The compounds or complexes of the present invention are produced by reacting (a) an alkoxylated amine of formula I with (b) phosphorous acid ($H_3PO_3$). Preferably, (c) a boron compound of formula II, or one or more of the other boron, compounds identified above, is added to the reaction mixture of (a) and (b). Where boron is to be included in the compounds or complexes of the invention, the reaction of the boron compound is preferably substantially simultaneous with the reaction of the alkoxylated amine and the organic phosphite, as contrasted to the two step process disclosed for similar reaction products of U.S. Pat. No. 4,529,528. That is, all three reactants are added together prior to carrying out the reaction.

However, the reaction may also be carried out in a two step process in the manner of U.S. Pat. No. 4,529,528, either by first reacting the amine with the phosphorous acid and then reacting the resulting product with the boron compound, or first reacting the amine with the boron compound and then reacting the phosphorous acid with this product. Such two step reactions have been found to yield soluble, though not as preferred compounds.

Although applicant does not wish to be bound to any single theory, it is believed that the reaction of (a) the alkoxylated amine of Formula I and (b) phosphorous acid proceeds as follows when w of Formula I is 0:

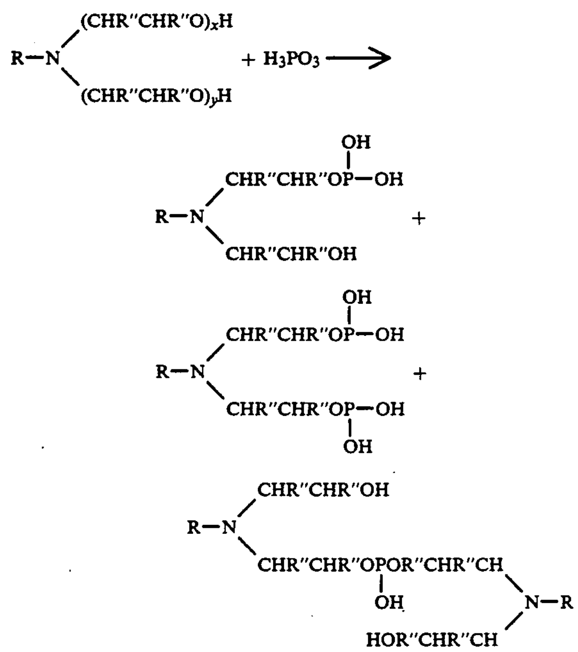

However, as will be evident to one skilled in the art from the present disclosure, other polymers and permutations of these reaction products may be formed. The reaction of (a) and (b) is carried out at a temperature of about 50° C. to about 250° C. and preferably, about 120° C. to about 180° C.

Preferably, (a) and (b) are reacted with (c) a boron compound selected from boric acid, a metaborate or a compound of the formula $$(R^3O)_mB(OH)_n \quad (II)$$

wherein $R^3$ is a $C_1$ to $C_6$ alkyl group, and m and n are about 0 to 3, their sum being 3. The reaction of (a), (b) and (c) proceeds at a temperature such as noted above for the reaction of (a) and (b). The optimum reaction time varies with the amount of boron used.

The products of the reaction of the alkoxylated amine of formula I with phosphorous acid, with or without the further addition of a boron compound, are highly effective in Falex EP tests in both oil and aqueous systems. However, these reaction products are somewhat viscous and only slightly soluble due to cross-linking, i.e., polymerization, in the product. Accordingly, it is preferred to modify the reaction in order to lower the viscosity and increase the solubility of the reaction product.

Therefore, preferably, (d) a monofunctional alcohol may be added to the reaction mixture in order to decrease the extent of polymerization in the final product. Appropriate monofunctional alcohols for use in the present invention are represented by formula III $R^4OH$ (III)

wherein $R^4$ is a hydrocarbon group of 1 to 30 carbons. Preferred monofunctional alcohols are $C_{18}$ to $C_{26}$ alkyl chain length alcohols.

The addition of such monofunctional alcohols to the mixtures of the present invention may somewhat reduce the Falex EP performance of the reaction product. However, adequate values, i.e., over 4,500 pounds, are obtained. In contrast, the solubility of these products increases greatly and their viscosity decreases compared to the reaction products of a and b or a, b and c alone.

Although not wishing to be bound by any particular theory, the present inventors believe the reaction of the alkoxylated amine of Formula I (wherein w is 0), phosphorous acid, and the monofunctional alcohol may be represented as follows:

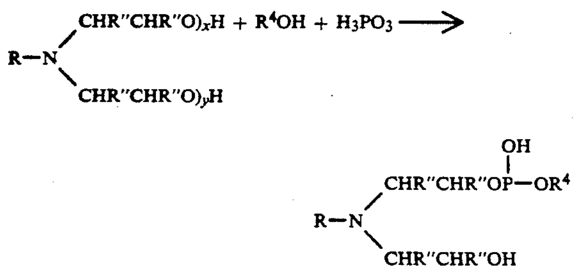

Again, it will be evident to one of ordinary skill in the art, that other products may be formed in this reaction and that other mechanisms or reaction routes may occur.

Alternatively, (e) a long-chain aliphatic carboxylic acid may be added to the reaction mixture in order to decrease the extent of polymerization in the reaction product. Appropriate long-chain aliphatic carboxylic acids are represented by formula IV $R^5COOH$ (IV)

wherein $R^5$ is a $C_1$ to $C_{30}$ hydrocarbon group. Preferably, the long-chain aliphatic carboxylic acid represented by formula IV is oleic acid.

The long-chain aliphatic carboxylic acid of formula IV may be first added to the alkoxylated amine and be allowed to react therewith. The long-chain aliphatic carboxylic acid will esterify one of the —OH groups on the amine. Then, the phosphorous acid is added to this mixture with any necessary additional alkoxylated amine in order to react all of the phosphorous acid. However, it is preferred that all of the reactants (i.e., the alkoxylated amine, the phosphorus acid and the carboxylic acid) be added together in one step. This one-step procedure results in a product having a higher Falex EP value than that of a two-step reaction.

The action of the long-chain aliphatic carboxylic acid on the present reaction products (wherein w of Formula I is 0) may be represented by the following non-limiting reaction scheme:

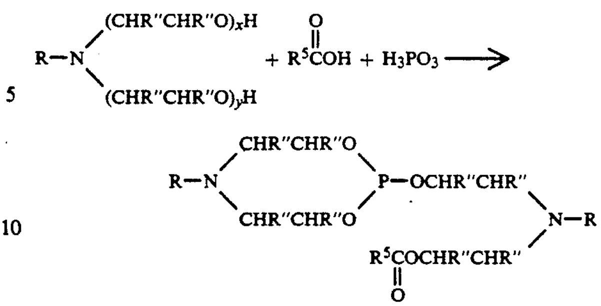

It will be evident to one skilled in the art, that other products may be formed by this reaction and that other mechanisms or reaction routes may occur.

The compounds or complexes of the present invention are referred to as reaction products since the exact structures of these compounds are not known. While applicants do not wish to be bound by any particular theory, it is believed that the reaction products are mixtures of a number of different simple and complex esters, including possibly cross-linked species and/or prepolymers. Thus, for example, the organic oxides of the boron compounds (when present) may react with one or both of the alkoxy groups of the alkoxylated amines to yield water and/or organic alcohol by-products.

The use of the long-chain aliphatic carboxylic acids of formula IV in combination with the alkoxylated amine and the phosphorous acid (and preferably, boric acid) results in a product having an increased Falex fail load and an increased 4-Ball EP LWI.

The preferred mole ratio of the alkoxylated amine, phosphorous acid and the monofunctional alcohol or long-chain aliphatic carboxylic acid, is 0.5:2 in any combination, and preferably 1:1:1.

The reaction of the various components described above, in any combination, proceeds readily under low to moderate heat, such as about 80° C. to 200° C., and preferably about 150° C. to 160° C. The optimum reaction time varies with the amount of boron being used, if any, but in general the reaction time should not exceed about 2½ to 3 hours, and the long reaction times of U.S. Pat. No. 4,529,528 should be avoided. During heating, the water formed as a by-product may be removed by azeotropic distillation, and the cessation of the evolution of water generally marks the end of the reaction. For products containing higher amounts of boron, 3 hours may be required, whereas for lesser amounts or no boron, 1.5 hours may be a sufficient reaction time. Moreover, the present reaction is preferably carried out in the presence of a nitrogen blanket.

The reaction may be carried out in the presence of a solvent, preferably a liquid hydrocarbon solvent such as toluene or xylene. Upon completion of the reaction the solvent and any by-product alcohol may be removed, e.g., by vacuum stripping. However, reactions in which there is a low amount of boron compound generally need no solvent, due to the small amount of water evolved by the esterification reaction. If desired, a nitrogen blanket may be used to help sweep out some of the higher alcohol by-products, particularly where no solvent is used.

The mix and nature of the reaction products will depend in part upon the proportion of the reactants contained in the reaction mixture. Molar ratios of alkoxylated amine to phosphorous acid in the range of about 0.1:1 to about 10:1 are believed to be satisfactory for the present invention, and ratios of about 0.5:1 to about 2:1 are preferred. Changing the relative amount of phosphorous acid compound in the reaction mixture in this manner tends to produce poorer results in the Falex EP test described below.

Where a boron compound is present in the reaction mixture, the molar ratio of alkoxylated amine to boron compound is in the range of about 30:1 to about 1:1. The ratio of phosphorous acid to boron compound is suitably in the range of about 0.5:1 to about 20:1, and preferably about 1:1 to about 15:1. The use of low amounts of boron compound generally obviates the need for a solvent for carrying out the reaction, but the presence of higher amounts of boron compound in the above range provides generally superior results in various metalworking tests and operations.

Alkoxylated amines which are useful in the present invention include, for example,
2-hydroxyethylhexylamine,
2-hydroxyethyloctylamine,
2-hydroxyethyldodecylamine,
2-hydroxyethyltetradecylamine,
2-hydroxyethylpentadecylamine,
2-hydroxyethyleicosylamine,
2-hydroxyethyltriacontylamine,
2-hydroxyethyloleylamine,
2-hydroxyethyltallowamine,
2-hydroxyethylsoyamine,
bis(2-hydroxyethyl)hexylamine,
bis(2-hydroxyethyl)octylamine,
bis(2-hydroxyethyl)dodecylamine,
bis(2-hydroxyethyl)tetradecylamine,
bis(2-hydroxyethyl)pentadecylamine,
bis(2-hydroxyethyl)eicosylamine,
bis(2-hydroxyethyl)triacontylamine,
bis(2-hydroxyethyl)oleylamine,
bis(2-hydroxyethyl)tallowamine,
bis(2-hydroxyethyl)soyamine,
2-hydroxylpropylhexylamine,
2-hydroxypropyloctylamine,
2-hydroxypropyidodecylamine,
2-hydroxypropyltetradecylamine,
2-hydroxypropylpentadecylamine,
2-hydroxypropyleicosylamine,
2-hydroxypropyltriacontylamine,
2-hydroxypropyloleylamine,
2-hydroxypropyltallowamine,
2-hydroxypropylsoyamine,
bis(2-hydroxypropyl)hexylamine,
bis(2-hydroxypropyl)octylamine,
bis(2-hydroxypropyl)dodecylamine,
bis(2-hydroxypropyl)tetradecylamine,
bis(2-hydroxypropyl)pentadecylamine,
bis(2-hydroxypropyl)eicosylamine,
bis(2-hydroxypropyl)triacontylamine,
bis(2-hydroxypropyl)oleylamine,
bis(2-hydroxypropyl)tallowamine,
bis(2-hydroxypropyl)soyamine and mixtures thereof.
Also included are the comparable members wherein in the above formula at least one of x and y is at least 2, as for example, 2-hydroxyethoxyethylhexylamine.

Preferred alkoxylated amines for use in the present invention are di-lower hydroxyalkyl alkyl amines in which the R group is preferably a $C_{10}$–$C_{20}$ hydrocarbon group or alkoxylated hydrocarbon group, and x, y and z are each 1. Preferred hydroxyalkyl groups are those in which R'' is hydrogen or methyl or mixtures thereof. Preferably, R' is a $C_1$ to $C_3$ alkylene group. Examples include 2-hydroxyethyl and 2-hydroxypropyl. Alkoxylated amines of this series are commercially available, for example, from Armak Chemical Company under the trademarks ETHOMEEN, PROPOMEEN and PROPODUOMEEN.

In addition to boric acid and the metaborates, the boron compounds useful in the present invention, include boric acid; mono-, di- and trimethyl borates; mono-, di- and tripropyl borates; mono-, di- and tributyl borates; mono-, di- and triamyl borates; mono-, di- and trihexyl borates; and silica borates. Boric acid is particularly preferred, primarily due to considerations of cost and availability.

Useful monofunctional alcohols for use in the present invention are, e.g., Exxal 18 and Exxal 26, by Exxon Chemicals which are synthetic alcohols of $C_{18}$ and $C_{26}$ chain length. Sylfat 96 oleic acid from Sealand Chemicals, may be preferably used as the long-chain aliphatic carboxylic acid in the present invention.

Compounds of the present invention in the acid pH range (below 7) are generally more effective in metalworking applications. Products in this pH range may suitably be achieved by raising the content of boron compound in the reaction mixture, as appropriate. On the other hand, the products should not be too highly acidic since this will result in corrosion of the metal being worked upon. In general, the compounds of the present invention are good rust inhibitors and do not require adjustment of acidity.

However, if a compound of the present invention has a pH of below about 5.5, it is desirable to adjust or pacify the pH to a range of about 5.5 to 7, and preferably 6 to 6.5, with an oil soluble amine. Suitable amines for adjustment of the pH include mixtures of long chain primary amines, which are commercially available from Rohm & Haas under the trademark PRIMENE 81R, or dimethyl decyl amine, which is commercially available from Ethyl Corporation under the trademark ADMA $C_{10}$. Other pacifiers include commercially available rust inhibitors which are well known to the art.

The compounds of the present invention are particularly useful as additives in various metalworking fluids to increase the lubricating capacity of the lubricating fluid and to reduce friction between metal parts. However, it will be understood by those skilled in the art that the compounds of the present invention will also have use in other lubricating environments, such as additives to engine and machinery lubricating oils.

The compounds appear to be useful for the full range of metalworking fluids from mineral oils to synthetic oils to the so-called soluble oils, the latter being emulsifiable in water for more preferred aqueous metalworking environments which provide greater cooling capacity to the metalworking operation. Thus, the additives of the present invention are readily soluble in and compatible with any of these metalworking fluids. Further, the compounds of the present invention may be used in conjunction with other metalworking fluid additives or formulation components, including sulfurized esters and active and passive sources of sulfur. Other additives, including corrosion inhibitors, surface active agents, thickeners for forming greases, and additives for specialized formulation uses, may also be included.

In general, the compounds of the present invention are soluble in paraffinic or naphthenic base stocks up to at least about 10 weight percent, which is the practical limit for use. When used in mineral oils or other synthetic lubricating oils, the compounds of the present invention are generally added in concentrations of about 0.1 to 10 weight percent, and typically about 1 to 6 weight percent. When used as additives to soluble oils which will be emulsified in aqueous metalworking formulations, the compounds of the present invention are added in concentrations of about 0.1 to about 20 weight percent, and preferably about 0.25 to about 10 weight percent.

The compounds of the present invention, when added to metalworking fluids, provide a high degree of lubricity in any of a wide variety of metalworking or machining operations, including broaching, threading, tapping, reaming, gear cutting, deep drilling, milling, boring and various automatic screw machine operations. However, the additives of the present invention are particularly advantageous in extreme pressure (EP) operations. When used to replace chlorinated paraffins or combinations of chlorinated paraffin with lard oil, the compounds of the present invention have been found to perform equally to or better than these conventional additives in a variety of lubricants, including drawing oils, tapping oils, gear oils and water-based metalworking formulations The invention will now be illustrated in more detail by reference to the following specific, non-limiting examples:

EXAMPLE I

To 247.5 g (0.48 mole) of Propomeen T/12 in a 1 liter three-necked flask fitted with an $N_2$ inlet, was added 26.6 g (0.324 mole) of $H_3PO_3$ over a 5 minute period at a temperature of 100°-110° C. The reaction mixture was heated at 110° C. for approximately 15 minutes. A very viscous gold colored liquid was obtained.

EXAMPLE II

A mixture of 149.4 g (0.391 mole) of bis-(2-hydroxypropyl)tallowamine (Akzo-Propomeen T/12) and 149.4g of Exxal 26 alcohol (0.381 mole), were heated to 100°-110° C. with agitation in a 1 liter three-necked flask. 28.8 g of phosphorus acid (0.351 mole) was then added to the mixture over a period of 5 minutes. The temperature of the reaction mixture then rose to 120° C. and was maintained at this temperature for 3 hours. After cooling to room temperature, 57.8 g (0.29 mole) of Primene 81R was added to this mixture over a period of 5 minutes. A viscous, gold colored liquid was obtained.

EXAMPLE III

A mixture of 93.4 g (0.33 mole) of oleyl alcohol and 25.75 g (0.33 mole) of $H_3PO_3$ was stirred and heated to 100° C. in a three-necked, 1 liter flask. To this mixture, 126.1 g (0.33 mole) of Propomeen T/12 was added dropwise over 30 minutes at 100°-120° C. The temperature of the resultant mixture was maintained at 110°-120° C. for an additional 2.5 hours. A viscous dark amber liquid product was obtained.

EXAMPLE IV 100 g of isostearyl alcohol (0.353 mole) was heated with agitation under an $N_2$ blanket to 90°-100° C. 28.95 g of phosphorus acid (0.353 mole) was then added and the resultant mixture was heated to 100°-110° C. for 15 minutes. 134.9 g (0.353 mole) of Propomeen T/12 was then added to this mixture over a period of about 30 minutes at 110°-120° C. The reaction mixture was held at this temperature for 1 hour. The product was a viscous gold colored liquid.

EXAMPLE V

To a 2 liter reactor fitted with a stirrer and an inlet for an $N_2$ blanket, was added 410.7 g (1.44 moles) of Exxal 18 alcohol. After heating to 100° C., 118.2 g (1.44 moles) of $H_3PO_3$ was added as quickly as possible. After heating this mixture for approximately 15 minutes, 550.5 g (1.44 moles) of bis-(2-hydroxypropyl)tallowamine (Propomeen T/12) was added dropwise at 100°-120° C. over a 30 minute period. The resultant reaction mixture was heated for an additional 30 minutes at 120°-125° C., for 60 minutes at 125°-130° C. and for 60 minutes at 150°-160° C. The resultant product was a viscous gold colored liquid.

EXAMPLE VI

A. To a 2 liter, three-necked flask equipped with a stirrer, a condenser, a Dean-Stark trap and an inlet for an $N_2$ blanket was added 519.8 g (1.36 moles) of Propomeen T/12 and 338.9 g (1.36 moles) of Sylfat 96 acid. This mixture was heated at 150°-180° C. until 14 ml of water was collected.

B. To a 1 liter reactor fitted with a stirrer and an inlet for an $N_2$ blanket were added 107 g (0.28 mole) of Propomeen T/12 and 184 g (0.28 mole) of the ester from part A. After heating this mixture to 150° C., 23 g (0.28 mole) of $H_3PO_3$ was added to the mixture. The resultant reaction mixture was heated and maintained at 150°-160° C. for 3.5 hours. A reddish-brown liquid was obtained.

EXAMPLE VII

A mixture of 142.3 g (0.373 mole) of Propomeen T/12, 244.8 g of the product of Example VI, Part A, and 1.3 g (0.021 mole) of boric acid was heated to 150° C. under a nitrogen blanket. To this mixture, 30.6 g (0.373 mole) of $H_3PO_3$ was then added as quickly as possible at 150°-165° C. The reaction mixture was maintained at 130°-150° C. for 3 hours. Upon cooling, a deep amber liquid product was obtained.

EXAMPLE VIII

To a one liter reactor fitted with a Dean-Stark trap was added 317.0 g (0.83 mole) of Propomeen T/12 and 10.5 g (0.17 mole) of boric acid. This mixture was heated to 150° C. under a nitrogen blanket After 6.5 ml of water had been collected in the Dean-Stark trap, 236.6 g (0.83 mole) of Exxal 18 alcohol was added to this mixture at a temperature of 145°-155° C. 68.1 g (0.83 mole) of $H_3PO_3$ was then added at a rate sufficient to maintain a reaction temperature of 150°-160° C. The reaction mixture was maintained at 150°-160° C. for an additional 2 hours. Upon cooling, a viscous deep amber liquid product was obtained.

EXAMPLE IX

A mixture of 280.3 g (0.73 mole) of bis(2-hydroxypropyl)tallowamine (Propomeen T/12) and 83.5 g (0.27 mole) of Sylfat 96 oleic acid was heated, under a nitrogen blanket, to 150° C. 36.9 g (0.45 mole) of $H_3PO_3$ was then added to this mixture in one portion. The reaction temperature was maintained at 150°-160° C. for 1.5 hours. Upon cooling, a gold colored liquid product was obtained.

TEST RESULTS

The products of Examples I-IX were tested in several standard tests which have been developed for metalworking fluids as described below. In these tests, the compounds of the invention were compared to one or more of the following standard or competitive lubricants on the market: (1) LUBRIZOL LZ-5347, a PEP metalworking additive containing carbonated alkyl benzene sulfonates; and (2) a standard additive formulation comprising 25% P145 chlorinated wax (40% chlorine) from Dover Chemical Corp. and 75% lard oil.

The additives tested were added to various oils identified below at the weight percentages indicated in the following Tables setting forth the results of each test.

In Tables I-III, the results of various wear tests are set forth using 1% to 5% (as indicated) of each additive dissolved in Exxon 150N mineral oil. The 4-Ball EP test (ASTM D-2783) measures the extreme pressure characteristics of a lubricant by a Load Wear Index (LWI) and a weld point. A test ball is rotated under load at a tetrahedral position on top of three stationary balls immersed in lubricant. Measurements of scars on the three stationary balls are used to calculate LWI's, and the weld is the load at which the four balls weld together in 10 seconds. The higher the values the better The 4-Ball Wear test (ASTM D-2266) measures the wear (displacement of metal by friction) when a test ball is rotated in a tetrahedral position on top of three stationary balls or discs. Wear is indicated by scar diameters on the three stationary balls or discs.

Falex EP Tests: In Tables II and III are given the results of tests on the Falex (FAVILLE-LeVALLY) lubricant tester, which is described for example in *United States Steel Lubrication Engineers Manual,* pages 136–137. In these tests, a brass pin revolves at 290 rpm between two steel blocks immersed in the oil while the pressure exerted between the blocks on the pin is increased until the brass pin fails, either by sudden shearing or wear occurring at a rate faster than the load can be increased. The failure load in p.s.i. is given with 4500 p.s.i. being the maximum test load. In the tests reported in Tables II and III, each additive was dissolved at a concentration of 5% in Exxon 150N mineral oil or in the case of the emulsion was prepared as for the Texaco chip test above (5% modified oil in water or 0.75% additive in the total emulsion).

In Table IV, the present compositions were tested according to ASTM D-665A, ASTM D-665B and the Cast Iron Chip Test for corrosion properties. In the two ASTM tests, a mixture of 300 ml of the mineral oil with 0.75 weight percent additive is mixed with 30 ml of distilled water (ASTM D-665A) or synthetic sea water (ASTM D-665B) at a temperature of 60° C. with two cylindrical steel specimens completely immersed therein for a period of 24 hours The specimens are observed for signs of rusting. Both test specimens in each test must be rust free in order to receive a passing report. In the chip test (Texaco Method No. ST-114), clean, dry, cast-iron chips are soaked in emulsions of a soluble oil, prepared by blending 15% of additive in Exxon 150N and emulsifying this blend at 5% in 100 ppm hardness water. The chips are then drained and spread evenly on the bottom of a Petri dish and are then allowed to dry and stand overnight in a controlled atmosphere. Out of 15 ml of standard test chips, 10 or fewer chips may have rust to receive a passing rating. Results are given as pass or fail.

Based on the test results shown in the attached Tables, the compounds of the present invention, when added to mineral oil lubricants, show excellent metalworking properties as well as good corrosion resistance. The test results compare very favorably to reference oils such as chlorinated wax plus lard oil additive. The tests indicate an optimum concentration of about 3 weight percent when added to the lubricant oils.

As can be seen in Tables II and III, the reaction products of Examples II–V (wherein the monofunctional alcohol is employed demonstrate a slightly lower Falex EP performance than Example I. However, the viscosity of these Examples was much lower while solubility was greatly increased.

In Examples VI and IX, a long-chain aliphatic carboxylic acid is reacted with the amine and phosphorous acid, increasing the Falex EP and 4-Ball EP LWI performance. The viscosity and solubility properties of these Examples were also improved over the products of the amine and phosphorous acid above.

The present invention may be embodied in other specific forms without departing from the spirit or the central attributes thereof and, accordingly, reference should be made to the appended claims, rather than to the foregoing specification as indicating the scope of the invention.

TABLE I

4-BALL WEAR TEST (3% Additive in Exxon ISO 46 Oil)

| Additive | Wear Scar (mm) |
|---|---|
| Example I | 0.29 |
| Exampl: II | 0.26 |
| Example III | 0.33 |
| Example IV | 0.39 |
| Example V | 0.37 |
| Example VI | 0.34 |
| Example VII | 0.33 |
| Example VIII | 0.42 |
| Example IX | 0.39 |
| Lubrizol 5347 | 0.31 |
| Chloroparaffin - Lard Oil | 0.45 |

TABLE II

EP TESTS

| Additive | Falex EP (5 wt. % Additive) (in Exxon 150 N) *Fail Load (lbs) | Torque at Fail | 4-Ball EP (3 wt. % Additive) (in Exxon 150 N) LWI | Weld |
|---|---|---|---|---|
| Example I | 5,000+ | 28–32 | 27.4 | 160 |
| Example II | 5,000+ | 30–35 | 41.8 | 200 |
| Example III | 4,500+ | 30–35 | 35.0 | 200 |
| Example IV | 4,600 | 30–35 | 34.7 | 200 |
| Example V | 4,800 | 30–35 | 36.0 | 200 |
| Example VI | >*5,500 | 30–35 | 41.8 | 200 |
| Example VII | 4,250 | 40–45 | 29.0 | 200 |
| Example VIII | 4,500+ | 45 | 32.2 | 250 |
| Example IX | 6,500 | 30–35 | 39.6 | 200 |
| Lubrizol 5347 | x4,100 | 95 | 27.6 | 160 |
| Chloroparaffin - Lard Oil | 4,500+ | 50 | 32.9 | 250 |

*Values over 4,500 are 'off scale' and are estimated values.
*Pin would not fail (no break).
xExcessive smoke and blackening of the pin and V blocks.

TABLE III

EP TESTS IN WATER BASED SYSTEMS (5% Additive in a Soluble Oil Base Diluted 19/1 with 100 ppm Water)

| Additive | Falex EP Fail Load, lbs. | Torque at Fail | 4-Ball EP LWI | 4-Ball EP Weld |
|---|---|---|---|---|
| Example I | 4,000 | 50-55 | 26.6 | 126 |
| Example II | 4,000 | 45-50 | 21.2 | 100 |
| Example III | 4,050 | 45-50 | 21.4 | 100 |
| Example IV | 4,300 | 45-50 | 26.0 | 126 |
| Example V | 4,550 | 45-50 | 26.1 | 126 |
| Example VI | 4,600 | 45-50 | 31.1 | 126 |
| Example VII | 4,250 | 40-45 | 17.7 | 100 |
| Example VIII | 2,750 | 45 | 17.8 | 100 |
| Example IX | 3,750 | 50-55 | 25.0 | 100 |
| Lubrizol 5347 | 4,050 | 70-75 | 29.6 | 126 |
| Chloroparaffin - Lard Oil | 3,750 | 55-60 | 25.7 | 100 |

TABLE IV

RUST TESTS

| Additive | ASTM D-665A | ASTM D-665B | Cast Iron* Chip Test |
|---|---|---|---|
| Example I | Pass | Fail | Fail |
| Example II | Fail | Fail | Pass |
| Example III | Pass | Fail (near Pass) | Pass |
| Example IV | Pass | Pass | Fail |
| Example V | Fail | Fail | Fail (near Pass) |
| Example VI | Pass | Pass | Pass |
| Example VII | Pass | Pass | Pass |
| Example VIII | Pass | Fail | Fail |
| Example IX | Pass | Pass | Pass |
| Lubrizol 5347 | Pass | Fail | Fail |
| Chloroparaffin - Lard Oil | Fail | Fail | Fail |

*5% additive in a soluble oil base, diluted 19/1 with water.

We claim:

1. A lubricant additive comprising the reaction product of (a) an alkoxylated amine of the formula

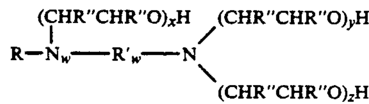

wherein R is a $C_6$ to $C_{30}$ hydrocarbon group or an alkoxylated $C_6$ to $C_{30}$ hydrocarbon group, R' is a $C_1$ to $C_6$ alkylene group and R" is individually hydrogen or a $C_1$ to $C_6$ hydrocarbon group, w is 0 or 1 and x, y and z are each integers of from 0 to 10, at least one of which is not 0, (b) phosphorous acid; wherein said reaction is carried out at a temperature of about 50° to 250° C. and the molar ratio of alkoxylated amine to phosphorous acid is about 0.1:1 to about 10:1, and (c) a compound selected from the group consisting of a boron compound which is selected from the group consisting of boric oxide, a metaborate, and a compound of the formula $$(R^3O)_mB(OH)_n \quad (II)$$

wherein $R^3$ is a $C_1$ to $C_6$ alkyl group, and m and n are 0 to 3, there sum being 3;

an alcohol of the formula $$R^4OH \quad (III)$$

wherein $R^4$ is a $C_1$ $C_{30}$ hydrocarbon group; and a long-chain aliphatic carboxylic acid of the formula $$R^5\underset{\substack{\|\\ O}}{C}OH \quad (IV)$$

wherein $R^5$ is a $C_1$ to $C_{30}$ hydrocarbon group.

2. A product according to claim 1, wherein the reaction product is the reaction product of (a) and (b) with (c) said boron compound.

3. A product according to claim 1, wherein the reaction product is the reaction product of (a) and (b) with (c) said alcohol.

4. A product according to claim 1, wherein the reaction product is the reaction product of (a) and (b) with (c) said long-chain aliphatic carboxylic acid.

5. A product according to claim 1, wherein the reaction of (a), (b) and (c) is substantially simultaneous.

6. A product according to claim 2, wherein said boron compound is boric acid.

7. A product according to claim 2, wherein the molar ratio of amine compound to boron compound in the reaction is about 30:1 to about 1:1.

8. A product according to claim 2, wherein the molar ratio of phosphorus acid to boron compound in the reaction is about 0.5:1 to about 20:1.

9. A product according to claim 1, wherein the reaction is carried out at a temperature of about 80° C. to about 200° C.

10. A product according to claim 1, wherein the reaction is carried out at a temperature of about 150° C. to about 160° C.

11. A lubricating composition comprising a major proportion of a lubricating oil and a friction reducing amount of a product of claim 1.

12. A method of lubricating a metalworking operation comprising performing said operation in the presence of a lubricating oil containing the product of claim 1.

* * * * *